US006132442A

United States Patent [19]

Ferragamo et al.

[11] Patent Number: 6,132,442

[45] Date of Patent: Oct. 17, 2000

[54] GRAFT CLAMP

[75] Inventors: Michael C. Ferragamo, North Dighton; Charles H. Brown, Jr., Wellesley; Aaron T. Hecker, Allston, all of Mass.

[73] Assignee: Smith & Nephew, Memphis, Tenn.

[21] Appl. No.: 09/276,300

[22] Filed: Mar. 25, 1999

[51] Int. Cl.[7] .......... A61B 17/122; A61F 2/08

[52] U.S. Cl. .......... 606/151; 623/13; 606/72

[58] Field of Search .......... 606/72, 73, 99, 606/151, 152, 157, 158; 623/13

[56] References Cited

U.S. PATENT DOCUMENTS

| | | | |
|---|---|---|---|
| Re. 34,871 | 3/1995 | McGuire et al. . | |
| D. 368,777 | 4/1996 | Goble et al. | D24/145 |
| D. 374,286 | 10/1996 | Goble et al. | D24/145 |
| D. 374,287 | 10/1996 | Goble et al. | D24/145 |
| D. 374,482 | 10/1996 | Goble et al. | D24/145 |
| D. 375,791 | 11/1996 | Goble et al. | D24/145 |
| 4,246,660 | 1/1981 | Wevers | 3/1 |
| 4,708,132 | 11/1987 | Silverstrini | 128/92 |
| 4,712,542 | 12/1987 | Daniel et al. | 606/96 |
| 4,793,335 | 12/1988 | Frey et al. | 128/92 R |
| 4,834,752 | 5/1989 | Van Kampen | 623/13 |
| 4,870,957 | 10/1989 | Goble et al. . | |
| 4,927,421 | 5/1990 | Goble et al. . | |
| 4,950,271 | 8/1990 | Lewis et al. | 606/102 |
| 4,960,420 | 10/1990 | Goble et al. | 606/72 |
| 4,988,351 | 1/1991 | Paulos et al. | 606/72 |
| 4,997,433 | 3/1991 | Goble et al. . | |
| 5,013,316 | 5/1991 | Goble et al. . | |
| 5,037,422 | 8/1991 | Hayhurst et al. . | |
| 5,037,426 | 8/1991 | Goble et al. . | |
| 5,108,431 | 4/1992 | Mansat et al. | 623/13 |
| 5,129,902 | 7/1992 | Goble et al. . | |

(List continued on next page.)

FOREIGN PATENT DOCUMENTS

| | | |
|---|---|---|
| 0 279 129 | 3/1991 | European Pat. Off. . |
| 2 590 792 | 5/1987 | France . |
| 196 49 450 A1 | 6/1998 | Germany . |
| 2 248 778 | 4/1992 | United Kingdom . |
| 2 288 739 A | 11/1995 | United Kingdom . |
| WO 96/41574 | 12/1996 | WIPO . |
| WO 98/11839 | 3/1998 | WIPO . |
| WO 98/22048 | 5/1998 | WIPO . |

OTHER PUBLICATIONS

"Washerloc Tibial Fixation Device for Soft Tissue Grafts," Arthrotek—an Integral Part of Biomers Worldwide Team, ©1997 Arthrotek, Inc., Warsaw, IN.

GeoFit™ Screw & Washer System, ©1997 Innovasive Devices, Inc., Marlborough, MA.

Techniques for ACL Reconstruction with Multi–Trac™0 Drill Guide, ©Acufex Microsurgical, Inc. 1994, Mansfield, MA.

Howell, "Why the Double–Looped Semitendinosus and Gracilis Graft is Effective at Restoring Stability and Function to the ACL Reconstructed Knee", pp. 1–9.

*Primary Examiner*—Paul J. Hirsch
*Assistant Examiner*—Michael B. Priddy
*Attorney, Agent, or Firm*—Fish & Richardson, P.C.

[57] ABSTRACT

A graft clamp for securing a tissue graft located within a tunnel in bone includes a first member having a first clamping face, and a second member having a second clamping face. The first and second members are sized for positioning at an opening of the tunnel such that the first and second clamping faces are positioned substantially transversely to a bone surface defining the tunnel opening to secure the tissue graft therebetween. The clamping faces have ridges. The first member includes a spike for insertion into the bone, and a collar for insertion into the opening of the tunnel. An attaching element, for example, a screw, attaches the second member to the first member. The clamping faces are located exterior to the tunnel with the attaching element extending into the tunnel. The position of the first member and the second member at the tunnel opening is maintained at least partially by tension applied to the tissue graft.

24 Claims, 7 Drawing Sheets

U.S. PATENT DOCUMENTS 5,129,906 7/1992 Ross et al. .
5,141,520 8/1992 Goble et al. .
5,147,362 9/1992 Goble .
5,209,756 5/1993 Seedhom et al. ........................ 606/151
5,211,647 5/1993 Schmieding .
5,314,427 5/1994 Goble et al. .............................. 606/72
5,344,421 9/1994 Crook ........................................ 606/61
5,350,380 9/1994 Goble et al. .
5,352,229 10/1994 Goble et al. .............................. 606/72
5,376,119 12/1994 Zimmermann et al. .................. 673/13
5,411,506 5/1995 Goble et al. .
5,411,523 5/1995 Goble .
5,425,733 6/1995 Schmieding .
5,425,767 6/1995 Steininger et al. ....................... 623/13
5,431,651 7/1995 Goble .
5,470,334 11/1995 Ross et al. .
5,527,342 6/1996 Pietrzak et al. .
5,562,671 10/1996 Goble et al. .
5,571,184 11/1996 DeSatnick ................................. 623/13
5,632,748 5/1997 Beck, Jr. et al. .
5,645,547 7/1997 Coleman .
5,649,963 7/1997 McDevitt .
5,702,397 12/1997 Goble et al. .
5,713,897 2/1998 Goble et al. .
5,718,706 2/1998 Roger ........................................ 606/73
5,720,753 2/1998 Sander et al. .
5,766,250 6/1998 Chervitz et al. .
5,769,894 6/1998 Ferragamo ................................ 623/13
5,782,866 7/1998 Wenstrom, Jr. ......................... 606/232
5,849,019 12/1998 Yoon ....................................... 606/157
5,961,520 10/1999 Beck, Jr. et al. ......................... 606/72
5,968,054 10/1999 Yeats, II et al. ........................ 606/120
6,022,348 2/2000 Daniel et al. ............................. 606/96

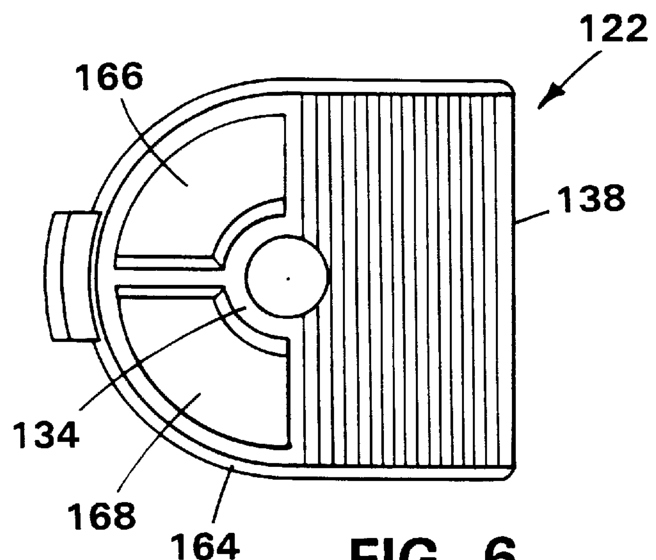
FIG. 6
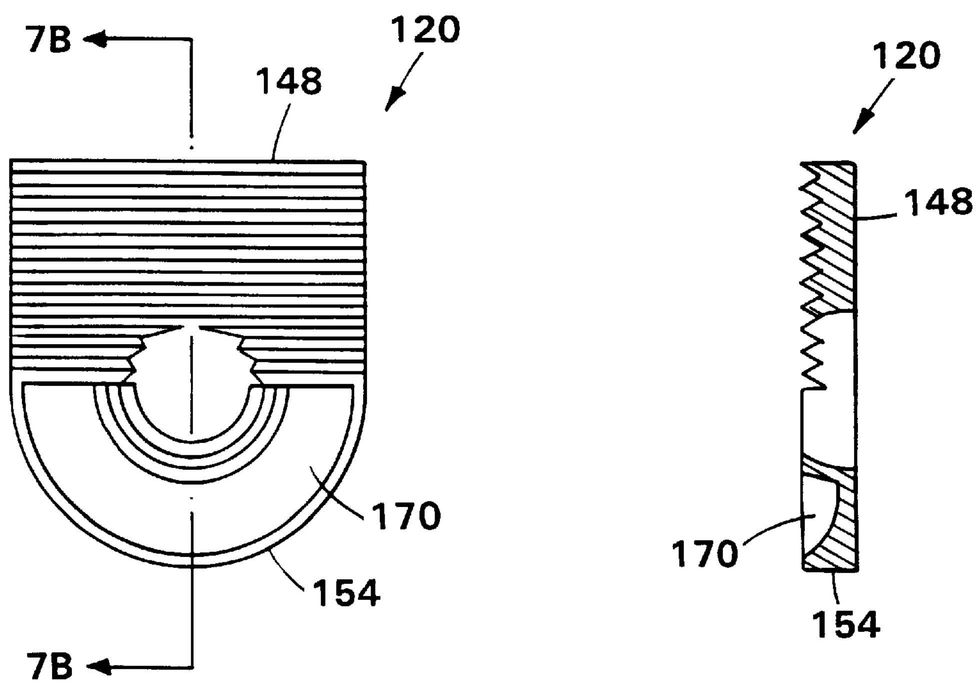
FIG. 7A
FIG. 7B

GRAFT CLAMP

BACKGROUND OF THE INVENTION

The invention relates to a graft clamp for securing a tissue graft.

A torn cruciate ligament is a common knee injury. One way to treat the injury is to replace the cruciate ligament with a tendon graft. Tunnels are drilled through the femur and tibia and the graft placed within the tunnels. One end of the graft is first fixed to the femur by a device which spans the tunnel opening, e.g., an endobutton described in Ferragamo, U.S. Pat. No. 5,769,894, entitled "Graft Attachment Device and Method of Attachment." The graft is then placed under tension, and the other end of the graft fixed to the tibia.

Known methods of fixing the graft to the tibia include attaching suture to the graft and using a screw positioned remote from the tunnel opening to secure the suture to the tibia. It is also known to position an interference screw within the tunnel in the tibia to fix the graft within the tunnel.

SUMMARY OF THE INVENTION

According to one aspect of the invention, a graft clamp for securing a tissue graft located within a tunnel in bone includes a first member having a first clamping face, and a second member having a second clamping face. The first and second members are sized for positioning at an opening of the tunnel such that the first and second clamping faces are positioned substantially transversely to a bone surface defining the tunnel opening to secure the tissue graft therebetween.

Embodiments of this aspect of the invention may include one or more of the following features.

The first clamping face has ridges. The first member includes a transverse element defining the first clamping face. The transverse element is substantially planar. The first member includes at least one spike extending from an opposing face on a side opposite the first clamping face for insertion into the bone.

The first member includes a collar extending from the opposing face of the transverse element for insertion into the opening of the tunnel. The collar is at an end region of the first member and the tissue graft is received over the collar around the end region. Alternatively, the collar is intermediate the ends of the first member and the first member defines an opening for receiving the tissue graft.

The second member is substantially planar. The second clamping face includes ridges. The second member defines an opening with a raised rim located about the opening and a dependent ledge extending over the first member for resisting rocking of the graft clamp. A spike extends from the clamping face of the second member for insertion into the bone.

The graft clamp includes an attaching element for attaching the second member to the first member. The second member defines an opening, and the first member defines an opening which is threaded. The attaching element is a screw which passes through the opening in the second member and threads into the opening in the first member.

According to another aspect of the invention, a graft clamp for securing a tissue graft located within a tunnel in bone includes a first member having a first clamping face, and a second member having a second clamping face. The first and second members are sized for positioning at an opening of the tunnel such that the first and second clamping faces are located exterior to the tunnel. An attaching element attaches the second member to the first member with the first clamping face opposing the second clamping face to secure the tissue graft therebetween.

Embodiments of this aspect of the invention may include one or more of the following features.

The attaching element is sized to extend into the tunnel. The first and second members are sized for positioning at an opening of the tunnel such that the first and second clamping faces are positioned substantially transversely to a bone surface defining the tunnel opening.

In another aspect, the invention features a method for securing a tissue graft to bone. The method includes locating the tissue graft within a tunnel formed in the bone, with an end of the tissue graft extending out of an opening of the tunnel. A first member having a first clamping face is positioned at the opening of the tunnel on a surface of the bone with the first clamping face transverse to the surface of the bone. Tension is applied to the tissue graft and the tissue graft is positioned over the first clamping face. A second member having a second clamping face is attached to the first member with the second clamping face transverse to the surface of the bone to secure the tissue graft between the first clamping face and the second clamping face.

Embodiments of this aspect of the invention may include one or more of the following features.

The positioning of the first member and the second member at the opening of the tunnel is maintained at least partially by the tension applied to the tissue graft. A spike on the first member is inserted into the bone to resist rotation of the first member with respect to the bone. The first and second members are attached with an attaching element.

Among other advantages, because the graft clamp is located at the opening of the tunnel in the bone formed for passage of the tissue graft, a second hole need not be formed in the bone for placement of the graft clamp. The clamp has a low profile so that it does not irritate the patient by extending far above the surface of the bone. The clamp does not extend far into the tunnel which could interfere with bone ingrowth during healing. Also, because the clamp is held in place at least partially by tension in the tissue graft, placement of the clamp is simplified.

Other features and advantages of the invention will be apparent from the following detailed description and from the claims.

BRIEF DESCRIPTION OF THE DRAWINGS

FIG. 6 is a top view of an alternative embodiment of a base clamp of a graft clamp;

FIGS. 7A and 7B are bottom and side views, respectively, of an alternative embodiment of a graft clamp washer;

DESCRIPTION OF THE PREFERRED EMBODIMENTS

Figure 1:
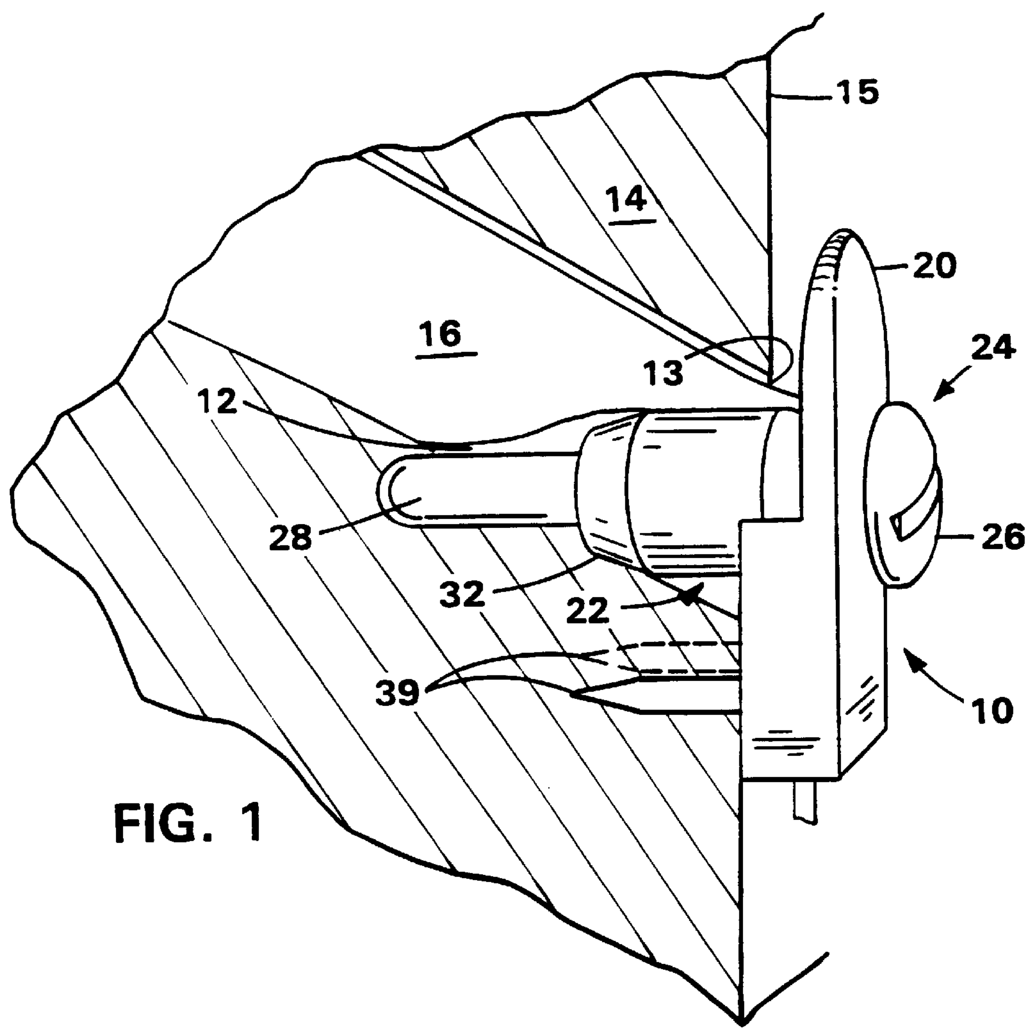
FIG. 1 is a diagrammatic illustration of a graft clamp shown positioned at a tibial tunnel.

Referring to FIG. 1, a graft clamp, e.g., a tibial clamp 10, is positioned at an opening 13 of a tibial tunnel 12 formed in a tibia 14. A tissue graft, e.g., graft tendon 16, extends through tibial tunnel 12 and is secured at tunnel opening 13 by tibial clamp 10. Tibial clamp 10 includes a first member, e.g., a base clamp 22, a second member, e.g., a washer 20, and an attaching element, e.g., a screw 24. Graft tendon 16 is routed from tibial tunnel 12 between base clamp 22 and washer 20 for securement therebetween.

Figure 2:
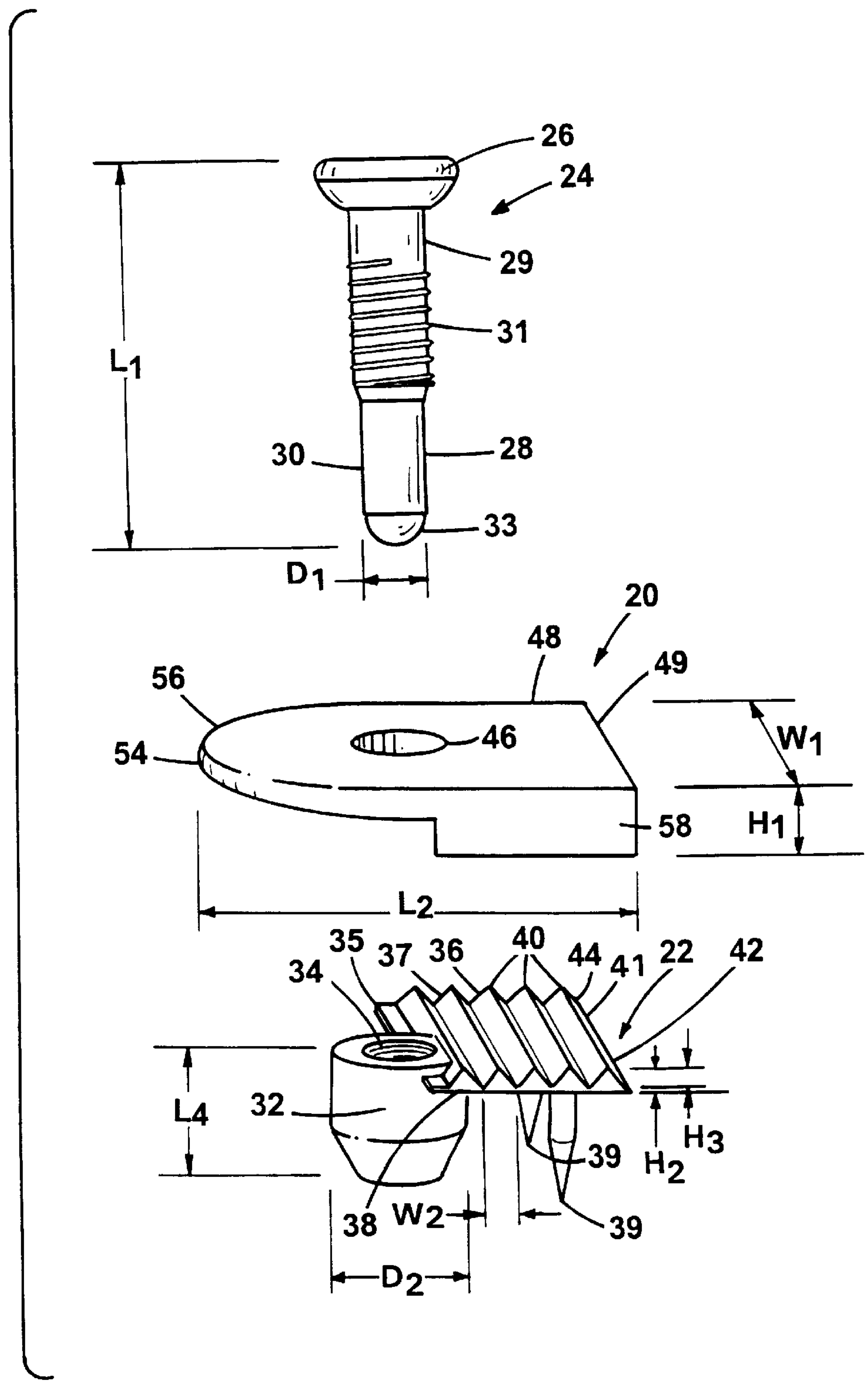
FIG. 2 is an exploded view of the graft clamp of FIG. 1.
Figure 3:
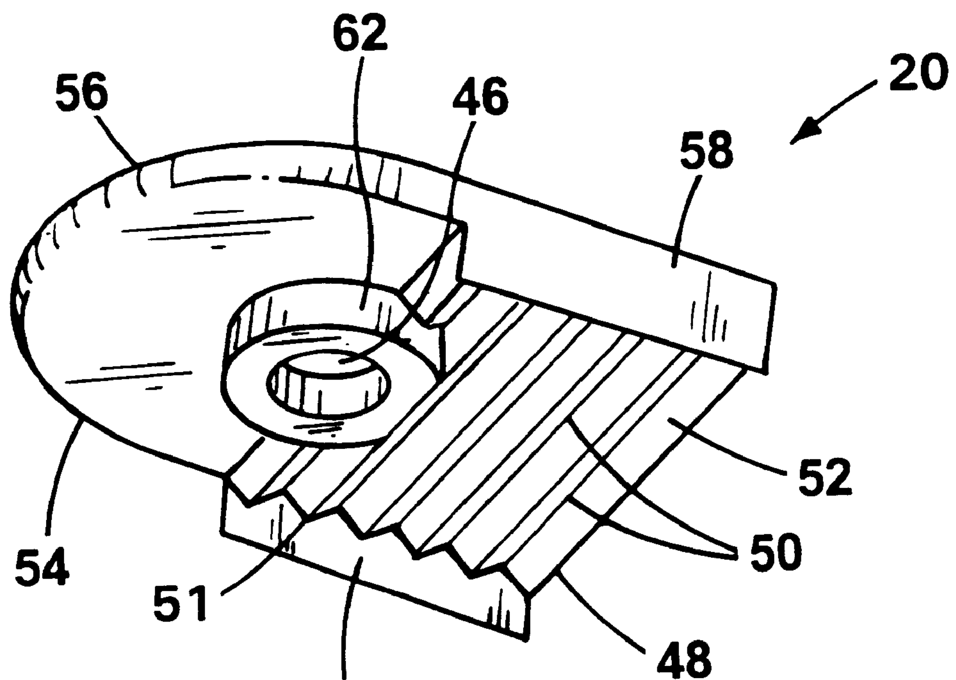
FIG. 3 is a perspective view of a graft clamp washer of the graft clamp of FIG. 1.
Figure 4:
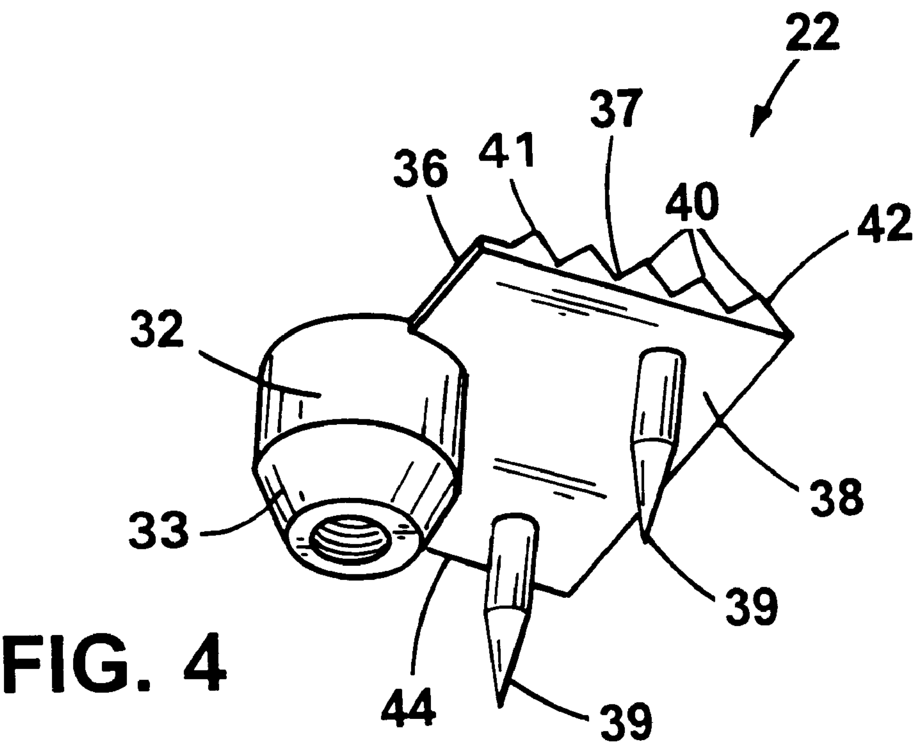
FIG. 4 is a perspective view of a base clamp of the graft clamp of FIG. 1.

Referring to FIGS. 2–4, washer 20 and base clamp 22 are secured together with screw 24. Screw 24 has a head 26 which is positioned outside tibial tunnel 12, and a shaft 28 which extends into tibial tunnel 12. Shaft 28 has a smooth proximal section 29 immediately below head 26 and a smooth distal section 30 at a distal end 33. Shaft 28 has threaded section 31 between smooth proximal section 29 and smooth distal section 30. Washer 20 defines a non-threaded opening 46 sized for receiving screw 24. Base clamp 22 has an annular collar 32 which extends into tibial tunnel 12 during use. Collar 32 has a frusto-conical end 33 and a threaded opening 34 sized to receive screw 24 and threadably engage screw threaded section 31.

Base clamp 22 has a transverse element 36 extending to one side of annular collar 32. Transverse element 36 has an upper clamping face 37, and washer 20 has a rectangular section 48 defining a lower clamping face 52. First clamping face 37 and second clamping face 52 are positioned at opening 13 of tunnel 12 (as opposed to remote from tunnel 12) substantially transversely to bone surface 15 (FIG. 1) defining tunnel opening 13 and exterior to tunnel 12 such that graft tendon 16 can be pulled over clamping face 37.

Figure 5:
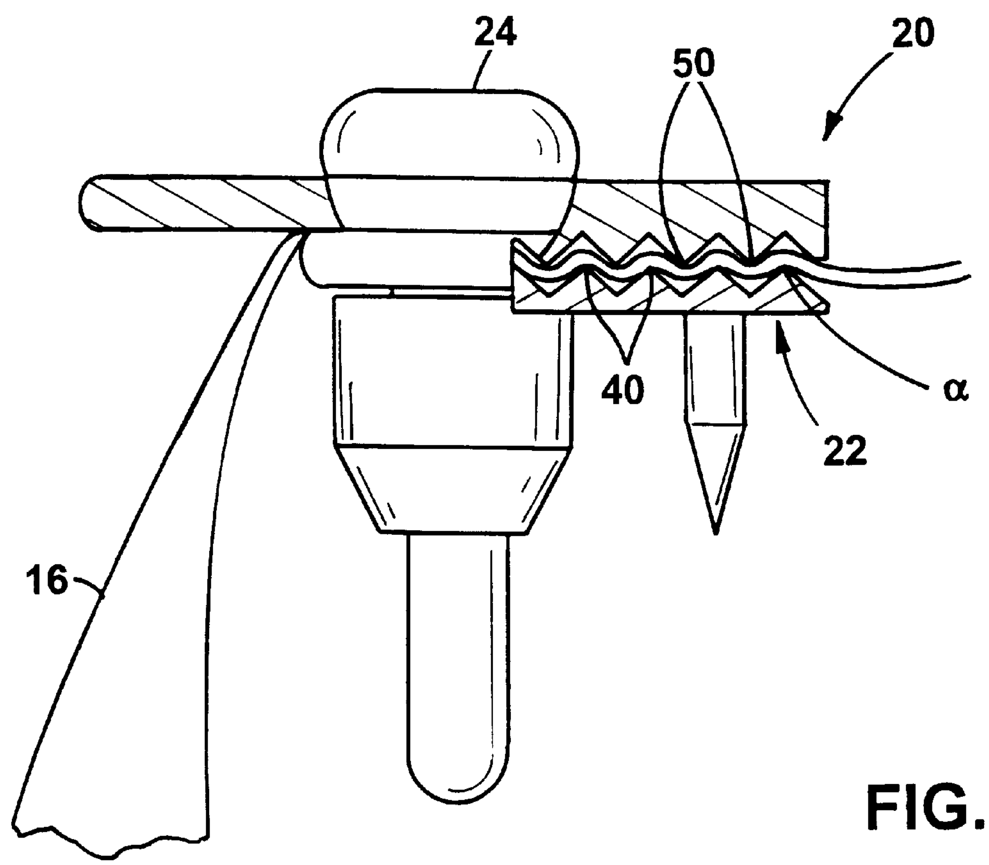
FIG. 5 is a partially cut-away side view of the graft clamp of FIG. 1.

Upper clamping face 37 defines ridges 40 extending between parallel sides 42 and 44, and lower clamping face 52 including corresponding ridges 50. Ridges 40 and 50 are of triangular cross-section with blunt edges 41, 51, respectively, to resist cutting the tissue graft. Ridges 40 and 50 are relatively off-set such that when openings 34 and 46 are aligned, ridges 40 and 50 mate. Graft tendon 16 is secured between ridges 40 and 50 as shown in FIG. 5. The circuitous path produced by ridges 40 and 50 provides traction for gripping graft tendon 16 to securely hold graft tendon 16 between base clamp 22 and washer 20.

Transverse element 36 has an opposing, lower face 38 with two spikes 39 extending from lower face 38 for insertion into the bone. Washer 20 has a flange 54 extending from first rectangular section 48. Flange 54 has a rounded smooth edge 56. Flange 54 minimizes rocking of clamp 10 relative to tibia 14. Extending from rectangular section 48 are two dependent ledges 58 and 60. Ledges 58 and 60 extend over parallel sides 42 and 44 of base clamp 22 when tibial clamp 10 is assembled to resist rotation of washer 20 with respect to base clamp 22. Adjacent to ridges 50 and partly encircling opening 46 is a raised rim 62. Rim 62 acts to resist rocking of washer 20 relative to tibia 14 and base clamp 22.

Referring to FIG. 2, to provide a low profile to the portions of clamp 10 which are positioned outside the tunnel, washer 20 is provided with an overall height, $H_1$, of, e.g., about 0.15" (3.8 mm), and transverse element 36 of base clamp 22 is provided with a height, $H_2$, of, e.g., about 0.04" (1 mm). For a bone tunnel diameter of about 10 mm, collar 32 has a diameter, $D_2$, of, e.g., about 0.29" (7.3 mm). Collar 32 has a length, $L_4$, of, e.g., about 0.335" (8.5 mm), which is long enough to provide a stable seat for base clamp 22 while not being too long such that it would penetrate the wall of the bone tunnel. Screw 24 is limited in length with an overall length, $L_1$, of, e.g., about 0.87" (22 mm), to minimize grazing of the screw against the bone wall while being long enough such that the threads of screw 24 engage the threads of collar 32 prior to tightening the screw. The diameter, $D_1$, of the portion of the screw extending below collar 32 is, e.g., about 0.13" (3.3 mm).

Washer 20 is sized to span across tunnel opening 13 to help stabilize clamp 10 under the tension applied by the graft tendon, minimizing any tendency of the clamp to rock relative to the tibia. Washer 20 has a length, $L_2$, of, e.g., about 0.9" (22.8 mm), and a width, $W_1$, of, e.g., about 0.8" (20 mm). Mating ridges 40 and 50 each have a height, $H_3$, of, e.g., about 0.04" (1 mm), a base width, $W_2$, of, e.g., about 0.08" (2 mm), and an angle, $\alpha$, of, e.g., about 90°.

In use, after the surgeon has drilled tunnels through the femur and tibia, placed a tissue graft through the tunnels, and fixed one end of the tissue graft to the femur, the surgeon tensions the tissue graft and fixes the second end of the graft to the tibia with graft clamp 10. The surgeon first positions base clamp 22 at tunnel opening 13 on a surface 15 (FIG. 1) of the tibia with collar 32 extending into the tunnel. Frusto-conical end 33 of collar 32 helps align collar 32 with opening 13 during insertion of the collar into the tunnel and provides a smooth advancing surface to prevent damage to graft tendon 16. Graft tendon 16 is located about collar 32 within tunnel 12 and extends out of the tunnel opening. The surgeon guides the graft tendon, which is formed of two or more strands, around an end region 35 of base clamp 22, around opening 34 in collar 32 (with one or more strands on either side of opening 34), and over clamping face 37.

While applying tension to graft tendon 16, the surgeon attaches washer 20 to base clamp 22 with screw 24 so that graft tendon 16 is secured between first clamping face 37 and second clamping face 52. First clamping face 37 and second clamping face 52 are positioned substantially transversely to bone surface 15 defining tunnel opening 13 and exterior to tunnel 12. Because tunnel 12 is drilled at an angle, e.g., about 40–70°, with respect to surface 15 of the bone and it is desired that base clamp 22 lie flat on bone surface 15 to provide a low profile, clamp 10 extends along tunnel 12 at an angle to the axis of tunnel 12.

Ledges 48 and 58 on washer 20 act to resist rotation of washer 20 with respect to base clamp 22, and rim 62 on washer 20 acts to resist rocking of washer 20 relative to tibia 14 and base clamp 22. Washer 20 spans across tunnel opening 13 to help resist rocking of clamp 10 relative to tibia 14.

Other embodiments are within the scope of the following claims.

For example, while spikes 39 are included on base clamp 22 to help hold base clamp 22 in place during fixation of the graft tendon, the spikes are not necessary to maintain graft clamp 10 in position during healing. Tension in graft tendon 16 tends to pull the graft clamp against the tibia to maintain graft clamp 10 in position during healing.

Referring to FIG. 6, in an alternative embodiment of a base clamp 122, a threaded collar 134 is intermediate the ends of the base clamp with a ridged section 138 on one side of threaded collar 134, and an extension frame 164 on a second side of collar 134. Frame 164 defines two openings 166 and 168 through which a graft tendon (not shown) can be threaded.

Referring to FIGS. 7A and 7B, a washer 120 for use with base clamp 122 also has an extension frame 154. Washer 120 has a ridged section 148 which mates with ridged section 138 of base clamp 122. Frame 154 defines a groove 170 for receiving the graft tendon (not shown) via openings 166, 168 in frame 164.

Figure 8:
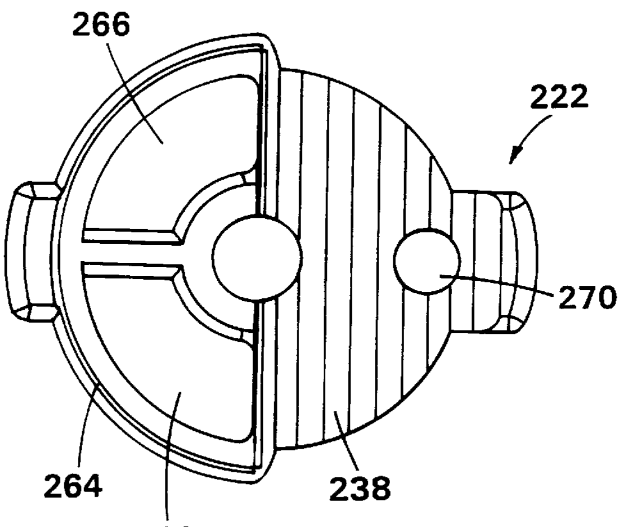
FIG. 8 is a top view of an additional alternative embodiment of a base clamp of a graft clamp.
Figure 9A:
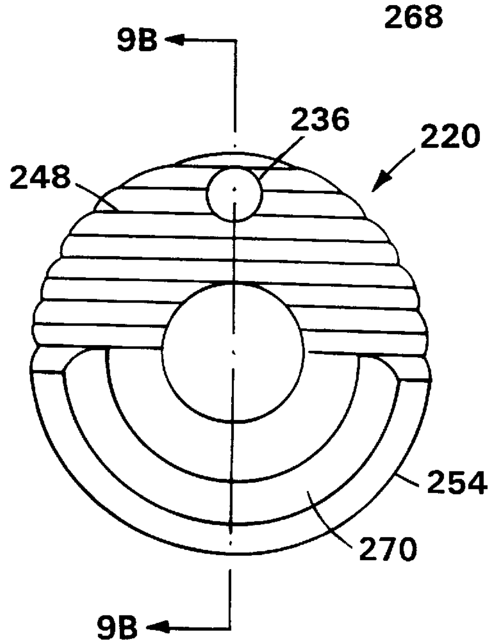
FIGS. 9A and 9B are bottom and side views, respectively, of an additional alternative embodiment of a graft clamp washer of a graft clamp.
Figure 9B:
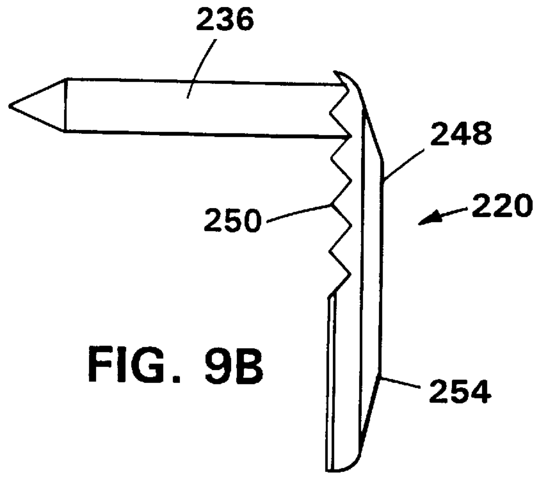

Referring to the embodiment shown in FIGS. 8, 9A and 9B, here a circular base clamp 222 defines an opening 270 for receiving a spike, and the spike 236 is located on a circular washer 220. Clamp 222 has, on one side of a threaded collar 234, a ridged, semi-circular section 238 and, on the other side of collar 234, an extension frame 264. Extension frame 264 defines two openings 266 and 268 through which a graft tendon (not shown) can be threaded. Washer 220 has a ridged section 248 for mating with ridged section 238 of clamp 222. Frame 254 defines a groove 270 for receiving the graft tendon (not shown) via openings 266, 268.

Figure 10:
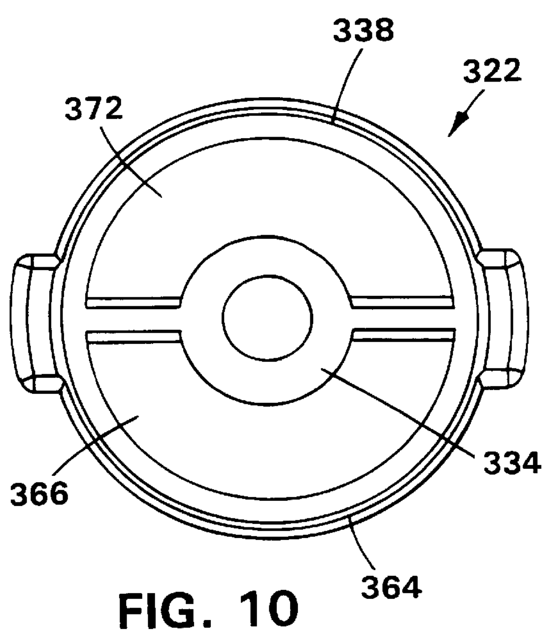
FIG. 10 is a top view of an additional alternative embodiment of a base clamp of a graft clamp.
Figure 11:
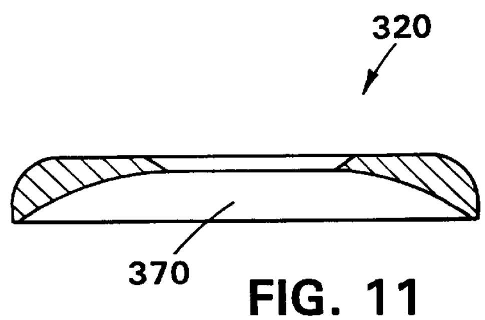
FIG. 11 is a cross-sectional side view of an additional alternative embodiment of a graft clamp washer of a graft clamp.

The graft tendon need not be threaded through the base clamp on only one side of the collar. Referring to FIG. 10, a base clamp 322 has, on one side of a threaded collar 334, a semi-circular section 338 defining an opening 372, and, on a second side of collar 334, a semi-circular section 364 defining an opening 366. Some strands of a graft tendon (not shown) are threaded through opening 366 while other strands are threaded through opening 372. A washer 320 for use with base clamp 322 is shown in FIG. 11. Washer 320 is circular and defines a groove 370 for receiving the graft tendon (not shown) via openings 372, 366.

What is claimed is:

1. A graft clamp for securing a tissue graft, the tissue graft being located within a tunnel in bone, the graft clamp comprising:

a first member having a first clamping face, and a second member having a second clamping face, the first and second members being sized for positioning at an opening of the tunnel such that the first and second clamping faces are positioned substantially transversely to a bone surface defining the tunnel opening to secure the tissue graft therebetween.

2. The graft clamp of claim 1 wherein the first clamping face includes ridges.

3. The graft clamp of claim 1 wherein the first member includes a transverse element defining the first clamping face, the transverse element being substantially planar.

4. The graft clamp of claim 3 wherein the transverse element defines an opposing face on a side opposite the first clamping face, the first member including at least one spike extending from the opposing face of the transverse element for insertion into the bone.

5. The graft clamp of claim 3 wherein the transverse element defines an opposing face on a side opposite the first clamping face, and the first member includes a collar extending from the opposing face of the transverse element for insertion into the opening of the tunnel.

6. The graft clamp of claim 5 wherein the collar is at an end region of the first member and the tissue graft is received over the collar around the end region.

7. The graft clamp of claim 5 wherein the collar is intermediate the ends of the first member and the first member defines an opening for receiving the tissue graft.

8. The graft clamp of claim 1 wherein the second member is substantially planar.

9. The graft clamp of claim 1 wherein the second clamping face includes ridges.

10. The graft clamp of claim 1 wherein the second member defines an opening and includes a raised rim located about the opening.

11. The graft clamp of claim 1 wherein the second member includes a dependent ledge extending over the first member.

12. The graft clamp of claim 1 wherein the second member includes a spike extending from the clamping face for insertion into the bone.

13. The graft clamp of claim 1 further comprising an attaching element for attaching the second member to the first member.

14. The graft clamp of claim 13 wherein the second member defines an opening, the first member defines an opening which is threaded, and the attaching element comprises a screw which passes through the opening in the second member and threads into the opening in the first member.

15. The graft clamp of claim 14 wherein the first member defines an opposing face on a side opposite the first clamping face, and the first member includes a collar extending from the opposing face of the first member for insertion into the opening of the tunnel, the collar defining the threaded opening.

16. A graft clamp for securing a tissue graft, the tissue graft being located within a tunnel in bone, the graft clamp comprising:

a first member including a substantially planar transverse element having a first clamping face defining ridges and an opposing face on a side opposite the first clamping face, a spike extending from the opposing face for insertion into the bone, and a collar extending from the opposing face for insertion into the opening of the tunnel, the transverse element defining a first opening and the collar defining a threaded throughbore aligned with the first opening, a second member including a second clamping face defining ridges, the second member defining an opening, and an attaching element for attaching the second member to the first member, the attaching element comprising a screw which passes through the opening in the second member and threads into the opening in the first member, the first and second members being sized for positioning at an opening of the tunnel such that the first and second clamping faces are positioned substantially transversely to a bone surface defining the tunnel opening with the ridges of the first clamping face and the second clamping face facing each other to secure the tissue graft therebetween.

17. A graft clamp for securing a tissue graft, the tissue graft being located within a tunnel in bone, the graft clamp comprising:

a first member having a first clamping face, a second member having a second clamping face, the first and second members being sized for positioning at an opening of the tunnel such that the first and second clamping faces are located exterior to the tunnel, and an attaching element for attaching the second member to the first member with the first clamping face opposing the second clamping face to secure the tissue graft therebetween.

18. The graft clamp of claim 17 wherein the attaching element is sized to extend into the tunnel.

19. The graft clamp of claim 17 wherein the first and second members are sized for positioning at an opening of the tunnel such that the first and second clamping faces are positioned substantially transversely to a bone surface defining the tunnel opening.

20. The graft clamp of claim 17 wherein the first clamping face includes ridges and the second clamping face includes ridges for securing the tissue graft therebetween.

21. A method for securing a tissue graft to bone, comprising:

locating the tissue graft within a tunnel formed in bone, an end of the tissue graft extending out of an opening of the tunnel, positioning a first member having a first clamping face at the opening of the tunnel on a surface of the bone with the first clamping face transverse to the surface of the bone, applying tension to the tissue graft, positioning the tissue graft over the first clamping face, and attaching a second member having a second clamping face to the first member with the second clamping face transverse to the surface of the bone to secure the tissue graft between the first clamping face and the second clamping face.

22. The method of claim 21 further comprising maintaining the positioning of the first member and the second member at the opening of the tunnel at least partially by tension applied to the tissue graft.

23. The method of claim 21 further comprising inserting a spike on the first member into the bone to resist rotation of the first member with respect to the bone.

24. The method of claim 21 wherein the step of attaching includes attaching the first member to the second member with an attaching element.

* * * * *

UNITED STATES PATENT AND TRADEMARK OFFICE
CERTIFICATE OF CORRECTION

PATENT NO. : 6,132,442
DATED : October 17, 2000
INVENTOR(S) : Michael C. Ferragamo et al.

It is certified that error appears in the above-identified patent and that said Letters Patent is hereby corrected as shown below:

Title page,
Item [73], assignee, please change "Smith & Nephew" to -- Smith & Nephew, Inc. --.
Item [56], U.S. PATENT DOCUMENTS, please change "2 248 778" to -- 2 248 778 A --.
Item [56], OTHER PUBLICATIONS, after "Multi-Trac™" delete "0".

Signed and Sealed this

Third Day of June, 2003

JAMES E. ROGAN
*Director of the United States Patent and Trademark Office*